US011206973B1

(12) United States Patent
Hiller

(10) Patent No.: US 11,206,973 B1
(45) Date of Patent: Dec. 28, 2021

(54) LARYNGOSCOPE

(71) Applicant: Kenneth Hiller, Houston, TX (US)

(72) Inventor: Kenneth Hiller, Houston, TX (US)

( * ) Notice: Subject to any disclaimer, the term of this patent is extended or adjusted under 35 U.S.C. 154(b) by 0 days.

(21) Appl. No.: 17/227,214

(22) Filed: Apr. 9, 2021

Related U.S. Application Data

(60) Provisional application No. 63/078,120, filed on Sep. 14, 2020.

(51) Int. Cl.
*A61B 1/267* (2006.01)
*A61B 1/00* (2006.01)
*A61B 1/06* (2006.01)

(52) U.S. Cl.
CPC .......... *A61B 1/267* (2013.01); *A61B 1/00009* (2013.01); *A61B 1/00013* (2013.01); *A61B 1/00016* (2013.01); *A61B 1/00027* (2013.01); *A61B 1/00066* (2013.01); *A61B 1/00165* (2013.01); *A61B 1/0661* (2013.01)

(58) Field of Classification Search
CPC combination set(s) only.
See application file for complete search history.

(56) References Cited

U.S. PATENT DOCUMENTS

| | | | | |
|---|---|---|---|---|
| 3,357,433 A | * | 12/1967 | Fourestier | A61B 1/00165 600/129 |
| 3,809,072 A | * | 5/1974 | Ersek | G02B 6/0008 600/249 |
| 3,835,841 A | * | 9/1974 | Terada | A61B 1/00165 600/157 |
| 3,901,220 A | * | 8/1975 | Koyasu | A61B 1/00165 600/176 |
| 4,489,728 A | * | 12/1984 | Matsuo | A61B 1/0052 600/146 |
| 4,576,147 A | * | 3/1986 | Hashiguchi | A61B 1/00165 600/129 |
| 4,592,343 A | * | 6/1986 | Upsher | A61B 1/07 600/188 |

(Continued)

FOREIGN PATENT DOCUMENTS

AU 2018361822 A1 4/2020
WO WO-2020/050922 A2 3/2020

*Primary Examiner* — Alexandra L Newton
*Assistant Examiner* — Jae Woo
(74) *Attorney, Agent, or Firm* — Foley & Lardner LLP

(57) ABSTRACT

A laryngoscope that includes a low-profile, straight laryngoscope blade that is thin and tapered in width and height, and designed to be intuitive in use and function. A distal tip of the blade may be configured to be placed in the anterior oropharynx with the angled camera (e.g., 10 degrees-40 degrees), thereby providing views of the airway and facilitating blade advancement. Real-time image data collected during a laryngoscopy may be communicated to a medical professional for immediate and ongoing feedback during a laryngoscopy or communicated to an electronic medical record. The laryngoscope provides first responders and airway managers of varying abilities a unique, portable, wireless laryngoscope to optimally manage airways and provide the greatest likelihood of safe, atraumatic airway access. The laryngoscope with the transformational laryngoscope blade design having an angled camera and wireless video forms a singular, effective instrument for airway managers and medical professionals.

13 Claims, 10 Drawing Sheets

(56) References Cited

U.S. PATENT DOCUMENTS

| | | | | |
|---|---|---|---|---|
| 4,846,154 A * | 7/1989 | MacAnally | A61B 1/00165 | 600/171 |
| 4,905,669 A * | 3/1990 | Bullard | A61B 1/267 | 600/104 |
| 4,947,829 A * | 8/1990 | Bullard | A61B 1/267 | 600/101 |
| 5,060,633 A * | 10/1991 | Gibson | A61B 1/267 | 600/193 |
| 5,261,392 A * | 11/1993 | Wu | A61B 1/267 | 128/200.26 |
| 5,381,787 A * | 1/1995 | Bullard | A61B 1/0056 | 600/188 |
| 5,527,262 A * | 6/1996 | Monroe | A61B 1/00142 | 348/66 |
| 5,643,221 A * | 7/1997 | Bullard | A61B 1/0056 | 604/188 |
| 5,772,581 A * | 6/1998 | Gaines | A61B 1/267 | 600/190 |
| 5,800,344 A * | 9/1998 | Wood, Sr | A61B 1/267 | 600/185 |
| 5,888,195 A * | 3/1999 | Schneider | A61B 1/267 | 600/199 |
| 6,123,666 A * | 9/2000 | Wrenn | A61B 1/05 | 434/262 |
| 6,292,221 B1 * | 9/2001 | Lichtman | G02B 7/08 | 348/345 |
| 6,354,993 B1 * | 3/2002 | Kaplan | A61B 1/07 | 600/188 |
| 6,490,490 B1 * | 12/2002 | Uchikubo | G16H 20/40 | 700/65 |
| 6,569,089 B1 * | 5/2003 | Covington | A61B 1/267 | 600/199 |
| 6,626,828 B2 | 9/2003 | Dohi et al. | | |
| 6,840,903 B2 | 1/2005 | Mazzei et al. | | |
| 6,929,600 B2 * | 8/2005 | Hill | A61B 1/00052 | 600/120 |
| 7,771,350 B2 * | 8/2010 | Geist | A61B 1/00032 | 600/199 |
| 7,946,981 B1 * | 5/2011 | Cubb | A61B 1/00052 | 600/194 |
| 8,251,898 B2 | 8/2012 | Pecherer | | |
| 8,529,442 B2 * | 9/2013 | Pacey | A61B 1/00142 | 600/188 |
| 9,066,700 B2 * | 6/2015 | McGrath | A61B 1/0623 | |
| 9,332,896 B2 | 5/2016 | Patel et al. | | |
| 9,386,914 B2 * | 7/2016 | Birnkrant | A61B 1/267 | |
| 9,949,629 B2 | 4/2018 | Gardner | | |
| 9,986,902 B2 * | 6/2018 | Tydlaska | A61B 1/00105 | |
| 10,286,171 B2 | 5/2019 | Gardner | | |
| 10,335,023 B2 | 7/2019 | Gardner | | |
| 10,588,498 B2 | 3/2020 | Dan et al. | | |
| 2001/0014768 A1 * | 8/2001 | Kaplan | A61B 1/00165 | 600/188 |
| 2002/0087050 A1 * | 7/2002 | Rudischhauser | A61B 1/07 | 600/199 |
| 2003/0078476 A1 * | 4/2003 | Hill | A61B 1/00052 | 600/160 |
| 2003/0181789 A1 * | 9/2003 | Mazzei | A61B 1/267 | 600/188 |
| 2003/0195390 A1 * | 10/2003 | Graumann | A61B 1/00016 | 600/188 |
| 2004/0215061 A1 * | 10/2004 | Kimmel | A61B 1/0607 | 600/179 |
| 2005/0148821 A1 * | 7/2005 | Berci | A61B 1/042 | 600/188 |
| 2005/0192481 A1 * | 9/2005 | Berci | A61B 1/00165 | 600/188 |
| 2005/0219376 A1 * | 10/2005 | Wittenberg | A61B 1/2673 | 348/222.1 |
| 2006/0020171 A1 * | 1/2006 | Gilreath | A61B 1/05 | 600/188 |
| 2006/0276694 A1 * | 12/2006 | Acha Gandarias | A61B 1/267 | 600/194 |
| 2007/0173697 A1 * | 7/2007 | Dutcher | A61B 1/2673 | 600/188 |
| 2007/0179342 A1 * | 8/2007 | Miller | A61B 1/267 | 600/188 |
| 2007/0197873 A1 * | 8/2007 | Birnkrant | A61B 1/05 | 600/160 |
| 2008/0004498 A1 * | 1/2008 | Pecherer | A61B 1/00032 | 600/193 |
| 2008/0064926 A1 * | 3/2008 | Chen | A61B 1/267 | 600/110 |
| 2008/0208006 A1 * | 8/2008 | Farr | A61B 1/0684 | 600/178 |
| 2009/0054727 A1 * | 2/2009 | Yamaya | G02B 23/2469 | 600/107 |
| 2009/0192350 A1 * | 7/2009 | Mejia | A61B 1/042 | 600/109 |
| 2009/0318758 A1 * | 12/2009 | Farr | A61B 90/53 | 600/112 |
| 2009/0322864 A1 * | 12/2009 | Karasawa | A61B 1/00183 | 348/65 |
| 2010/0022843 A1 * | 1/2010 | Pecherer | A61B 1/00055 | 600/197 |
| 2010/0041955 A1 * | 2/2010 | Grey | A61B 1/06 | 600/212 |
| 2010/0198009 A1 * | 8/2010 | Farr | A61B 90/53 | 600/109 |
| 2011/0060190 A1 * | 3/2011 | Pecherer | A61B 1/00179 | 600/188 |
| 2011/0077466 A1 * | 3/2011 | Rosenthal | A61B 1/042 | 600/188 |
| 2011/0144436 A1 * | 6/2011 | Nearman | A61B 1/267 | 600/188 |
| 2012/0330104 A1 * | 12/2012 | Tenger | A61B 1/0684 | 600/191 |
| 2013/0197312 A1 * | 8/2013 | Miller | A61B 1/00045 | 600/188 |
| 2014/0135582 A1 * | 5/2014 | Selcho | A61B 1/267 | 600/188 |
| 2015/0080655 A1 * | 3/2015 | Peterson | A61B 1/00105 | 600/112 |
| 2016/0242637 A1 * | 8/2016 | Tydlaska | A61B 1/00101 | |
| 2017/0273539 A1 * | 9/2017 | Law | A61B 1/00002 | |
| 2018/0338675 A1 * | 11/2018 | Eggli | A61B 1/00055 | |
| 2020/0113427 A1 * | 4/2020 | Molnar | A61B 1/0676 | |

\* cited by examiner

LARYNGOSCOPE

RELATED APPLICATIONS

This application claims priority to U.S. Patent Application having Ser. No. 63/078,120 filed on Sep. 14, 2020, the contents of which are incorporated hereby by reference in their entirety.

BACKGROUND OF THE INVENTION

A laryngoscopy is an endoscopy of the larynx, which is part of the airway. Laryngoscopies are medical procedures performed to obtain a view of the vocal cords and the glottis, the anatomical region through which an endotracheal intubation is performed. Laryngoscopy is done routinely to facilitate endotracheal intubation during general anesthesia for surgery or emergently to secure the airway during cardiopulmonary resuscitation.

There are two basic types of laryngoscope blades currently commercially available: curved blades and straight blades. Curved blades are more commonly used than straight blades, since curved blades are wider and stabilize the tongue to a greater degree than narrower straight blades. Curved blades, however, are more difficult to insert and given their design cannot compress the tongue as well as straight blades, in part due to their curvature and thickness.

SUMMARY OF THE INVENTION

To overcome inherent design shortcomings of laryngoscopes with either conventional curved or straight laryngoscope blades, a laryngoscope blade may be configured to perform a hybrid of functions of curved and straight blades. This laryngoscope, which may be a portable, wireless videolaryngoscope may include the blade with the hybrid of functions so as to allow airway managers of varying abilities the greatest likelihood of obtaining safe, atraumatic airway access. To provide for the hybrid of functions, the blade may be a low-profile, straight laryngoscope blade that is thin (both along the lateral and vertical axes) and tapered (e.g., 2:1 ratio of lateral width from handle to tip, and 2.5:1 ratio of vertical width from handle to tip), designed to be intuitive in use and function. It should be understood that alternative configurations of the laryngoscope blade that provide the same or similar functionality may be utilized.

Contrary to traditional straight blades, which are designed to lift the epiglottis, the blade may include an angled camera (i.e., a camera at an angle relative to a longitudinal axis along the blade (e.g., of the blade)) to visualize the airway prior to advancing and adjusting the position of the blade during use. The geometry and angled camera of this straight laryngoscope blade make the blade easy to use, thereby simplifying viewing and enhancing patient safety. The distal tip of the blade may be configured to be placed in the anterior oropharynx of a patient with the angled camera providing unprecedented views of the airway and facilitating blade advancement. Depending on a patient's anatomy, lifting the epiglottis prior to placement of an endotracheal tube may or may not need to be performed when using the blade.

Unlike currently available straight and curved blades, the tapered blade design provides a stable base to lift and compress the tongue for an unparalleled, unobstructed linear path to the airway. The laryngoscope with the low-profile, straight, tapered blade has civilian and military applications that enable airway managers of varying abilities the greatest likelihood of safe, atraumatic airway access.

In summary, a laryngoscope blade design may provide for hybrid functionality of both straight and curved blade designs and include an angled camera (i.e., a camera oriented in an offset angle below a longitudinal axis of the blade to capture images of a scene). A laryngoscope using the blade may be configured to capture and communicate video wirelessly and in real-time so as to form a singular, effective instrument for airway managers.

One embodiment of a method of manufacturing a laryngoscope may include forming a blade being straight and having a handle side and a non-handle side. The blade extends from a proximal end to a distal end, and may be configured to connect to a handle at the proximal end. A first channel configured to enable light signals to pass therethrough through the blade may be formed, where the first channel may include (i) a first aperture disposed at the proximal end of the first channel and (ii) a second aperture disposed at the distal end of the first channel. A second channel configured to enable optical signals to pass therethrough may be formed, the second channel may include (i) a third aperture disposed at the proximal end of the second channel and (ii) a fourth aperture disposed at the distal end of the second channel, where the fourth aperture may be oriented at an offset angle on or toward the handle side such that images captured via the fourth aperture are at the offset angle.

An embodiment of a laryngoscope may include a blade being straight and having a handle side and a non-handle surface. The blade extends from a proximal end to a distal end. A handle may be configured to be connected to the blade at the proximal end and extend on or toward the handle side of the blade. The handle may define a cavity in which electronics are positioned. An illumination source may be configured to illuminate a scene. A camera may be configured to capture images of the scene illuminated by the illumination source, the scene may be at an offset angle on the handle side of the blade.

BRIEF DESCRIPTION OF THE DRAWINGS

Illustrative embodiments of the present invention are described in detail below with reference to the attached drawing figures, which are incorporated by reference herein and wherein.

DETAILED DESCRIPTION OF THE INVENTION

A laryngoscopy is an endoscopy of the larynx, which is part of the airway/trachea. Laryngoscopies are medical procedures performed to obtain a view of the vocal cords and the glottis, the anatomical region through which an endotracheal intubation is performed. Laryngoscopy is done routinely to facilitate endotracheal intubation during general anesthesia for surgery or emergently to secure the airway during cardiopulmonary resuscitation. Compared to existing curved and straight laryngoscope blades, this de novo, low profile laryngoscope blade simplifies blade insertion, increases tongue stability, maximizes tongue compression, and has an angled camera that combine to simplify views and access to the vocal chords and glottis.

Figure 1:
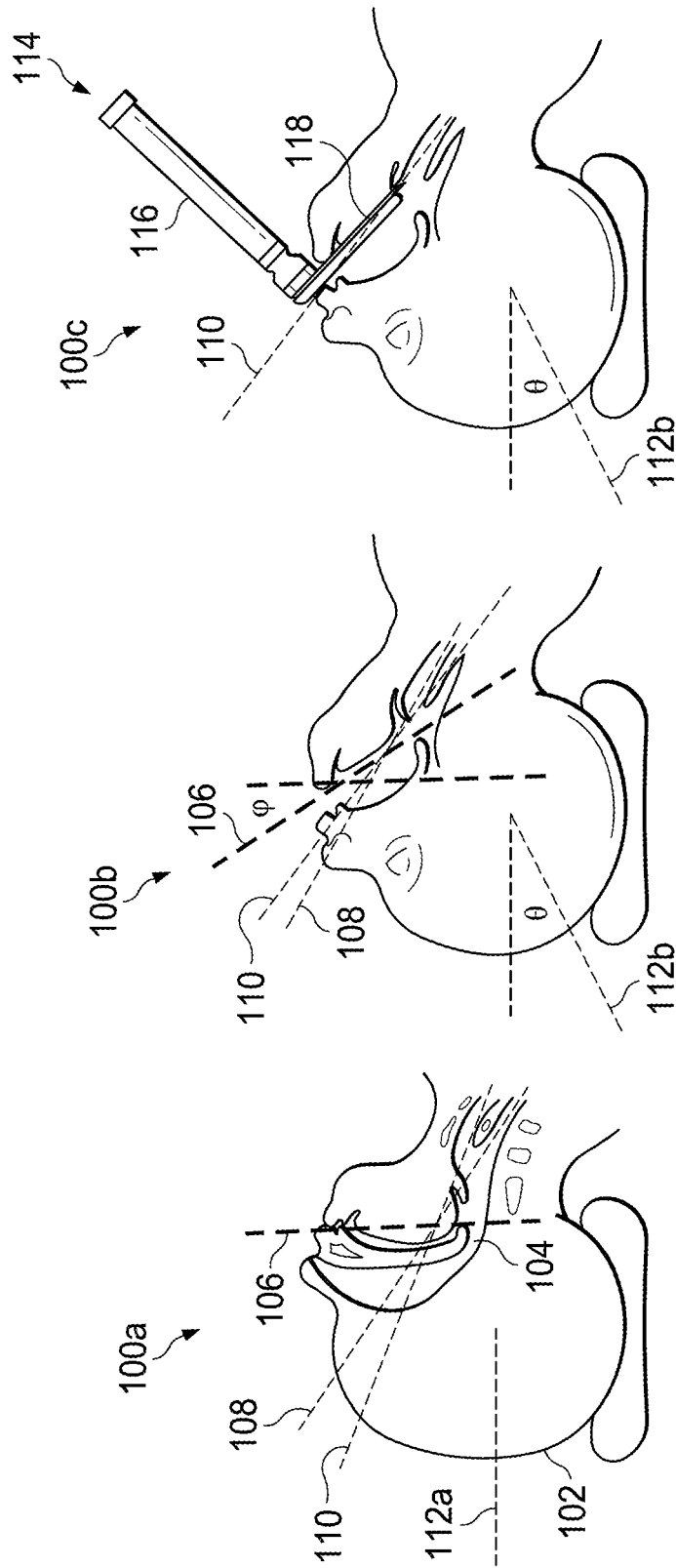
FIG. 1 are illustrations of illustrative scenes including a head of a patient.

With regard to FIG. 1, a routine, direct laryngoscopy with a straight blade is illustrated in illustrative scenes 100a-100c are shown. A head 102 includes an airway 104 in which an oral axis 106, pharyngeal axis 108, and tracheal axis 110 are defined. The head 102, which has a baseline head axis 112a when neutrally aligned with the spine is at 0 degrees. When airway managers perform a direct laryngoscopy, the airway managers may rotate the head 102 to have a head axis 112b at an angle (θ). By rotating the head 102 and/or lifting the tongue, the airway 104 is adjusted such that the tracheal axis is more readily aligned with a laryngoscope 114 that includes a handle 116 and laryngoscope blade 118 that is mounted to the handle 116, as shown in scene 100c.

The laryngoscope blade 118 is a conventional straight blade, which includes a light (not shown) oriented along the longitudinal axis of the blade 118. Routine direct laryngoscopy with a straight blade is typically done with the patient lying on his/her back and involves the following: rotation of the head, such that the oral axis rotates (φ) degrees, insertion of the laryngoscope into the mouth on the right side, sweeping the blade to the left to move the tongue and visualize the airway. Patient anatomy and clinical conditions may make laryngoscopy challenging with currently available laryngoscopes. As shown, in order to position the laryngoscope blade 118 in a position that enables a medical professional to view the airway, the head is rotated and the blade is oriented in a manner that is difficult for both the medical profession and patient, especially in the event when the patient has neck or other head trauma.

Figure 2:
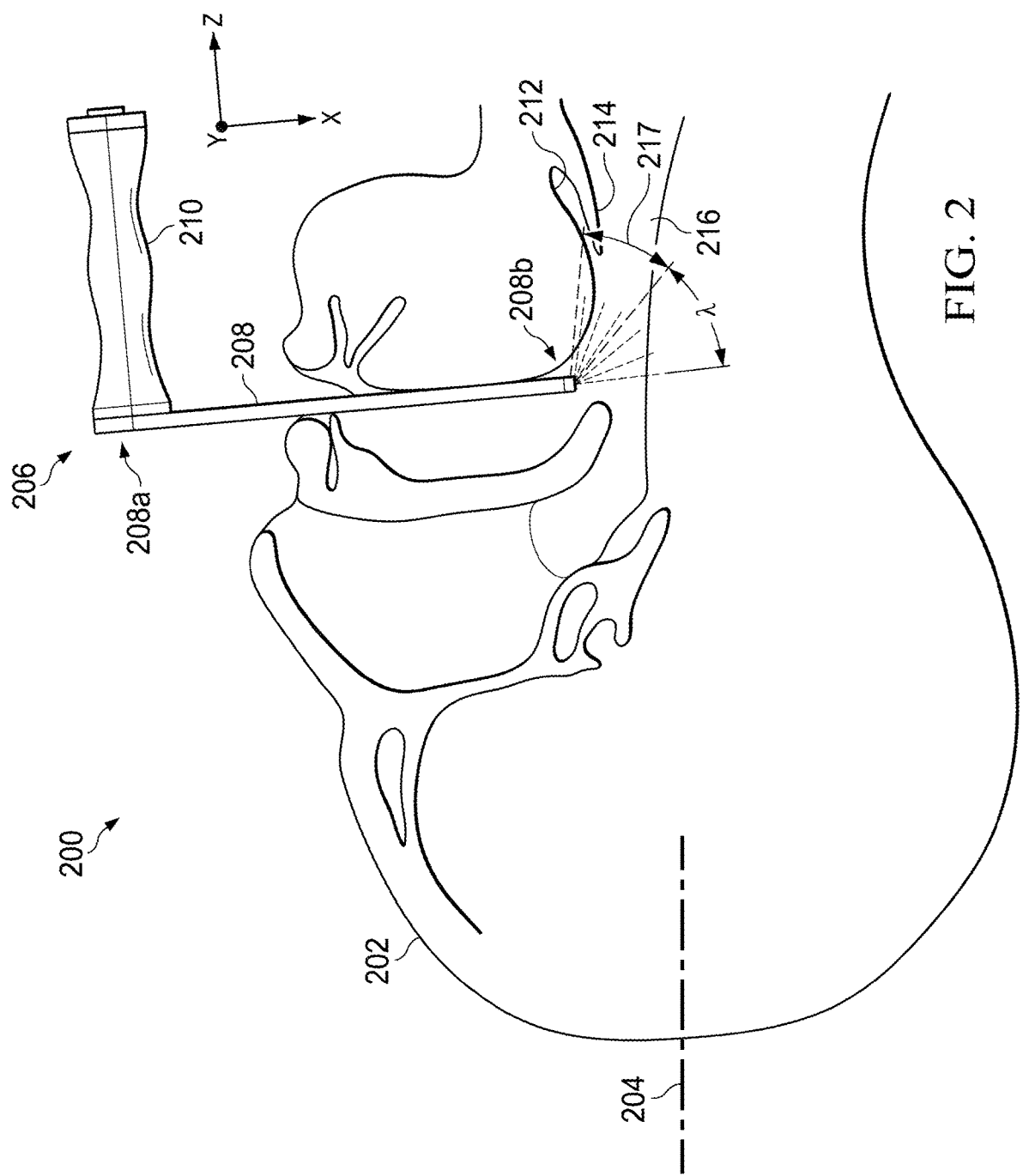
FIG. 2 is an illustration of an illustrative scene in which a patient is lying down with a baseline head axis being neutral with the spine (i.e., 0 degrees) is shown with an illustrative laryngoscope positioned within his or her airway.

With regard to FIG. 2, a supine patient is illustrated in the scene 200 in which a patient 202 is lying down with a baseline head axis 204 being neutral with the spine (i.e., 0 degrees) is shown with an illustrative laryngoscope 206 including a blade 208 positioned within his or her mouth/anterior oropharynx. The laryngoscope 206 includes a handle 210 and low profile, tapered straight laryngoscope blade 208. Conventional curved laryngoscope blades are inserted into the vallecula 212. Conventional straight laryngoscope blades are designed to lift the epiglottis 214. Depending on a patient's anatomy, lifting the epiglottis 214 prior to placement of an endotracheal tube into the airway/trachea 216 may or may not be required with this blade 208. The blade 208 is connected to the handle 210 at a proximal end 208a and a camera (not shown) and illumination source (not shown) may be projected at a distal end 208b of the blade 208. The camera and illumination source may be at an angle (k), which may range from 10 degrees to 40 degrees, for example, relative to a longitudinal axis X along the blade 208. In an embodiment, the angle may be fixed at approximately 20 degrees and the field-of-view may be +/−10 degrees, thereby providing an airway manager a viewing angle between 10 and 30 degrees. As shown, an illustrative view an illumination field-of-view 217 extends below the blade 208 so as to enable the airway manager to perform a laryngoscopy with the patient's head 202 at the baseline head axis 204, which may enable endotracheal intubation even with challenging patient anatomy. In an alternative embodiment, the angle of the camera and illumination source may be selectable and/or adjustable by an airway manager.

Figure 3A:
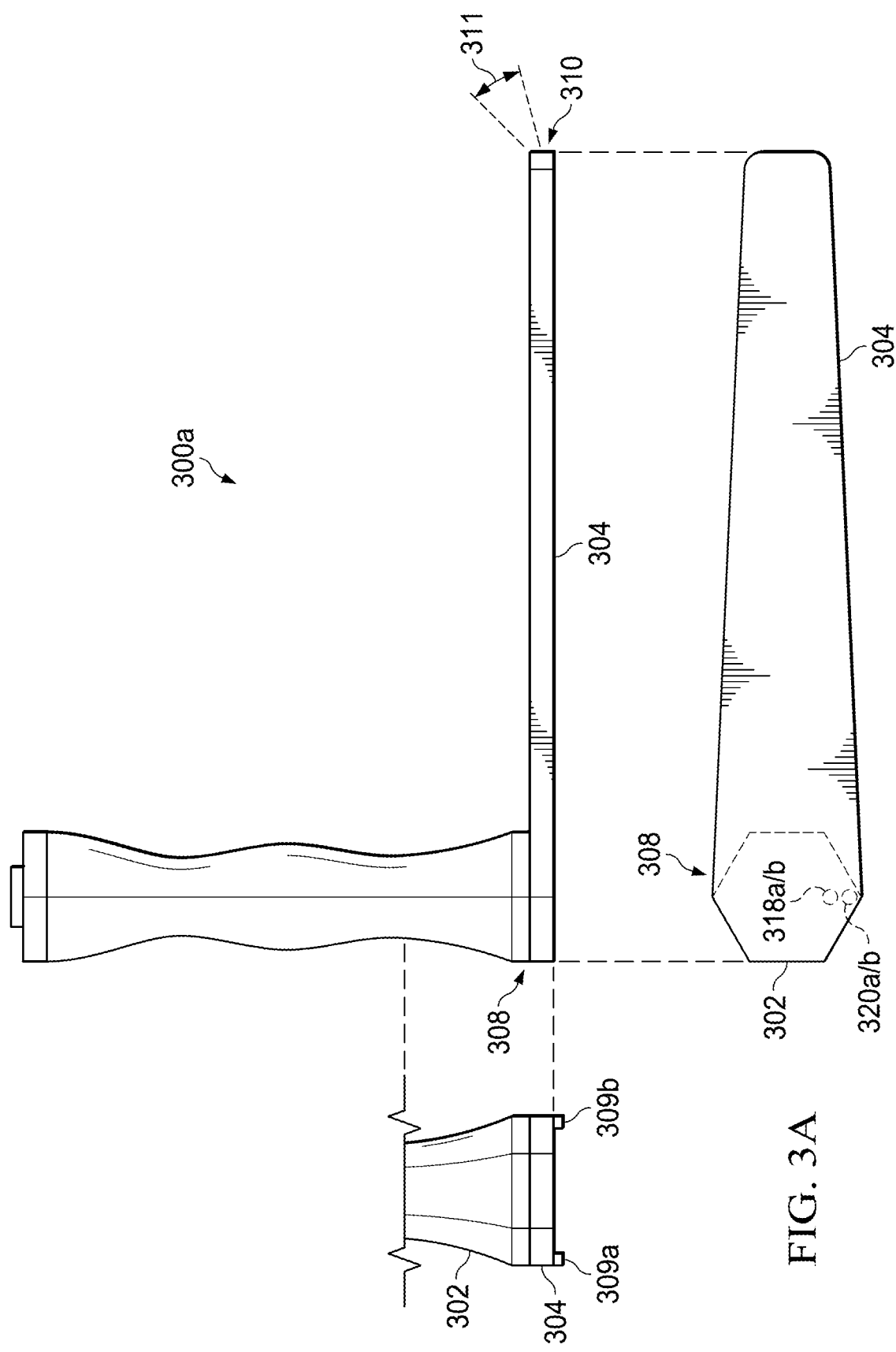
FIGS. 3A-3E are illustrations of an illustrative laryngoscope according to the principles described herein.

With regard to FIG. 3A, a side view illustration of an illustrative laryngoscope 300a is shown. The laryngoscope 300a is shown to include a handle 302 removably connected to a laryngoscope blade 304. The handle 302 may have a length of approximately 80 mm with a grip 306 having a cylindrical or other shaped grip that is comfortable for an airway manager. The handle 302 defines a cavity in which electronics and an energy source, such as a rechargeable battery, may be stored. In an embodiment, a connection 308 between the handle 302 and blade 304 may include multiple apertures, including one for an optical path for a camera to capture images and another for a light path for an illuminator to project a light from the handle 302 through the blade 304. In an alternative embodiment, an illuminator and/or camera may be positioned in or on the blade 304.

In an embodiment, the blade 304 may taper in width and/or thickness along the z-axis (i.e., from handle connection 308 (i.e., the proximal end) to the tip 310 (i.e., the distal end)). The taper may be defined by a taper ratio (e.g., widest to narrowest distance). For example, the thickness of the blade 304 may be about 2.5 mm at the connection 308 and about 1 mm at the tip 310. It should be understood that alternative thicknesses and taper ratios may be utilized. The thickness enables conduits, one for an optical path (e.g., optical tubes) for a camera and one for a light path for an illumination source, to extend therethrough, as further provided herein. Although shown to be flat, it should be understood that the straight blade 304 may taper in thickness such that the blade 304 is thicker at the handle end than at the tip 310. Because this blade is low profile and thinner than currently available straight blades, there is more room for the airway manager to maneuver and compress the tongue to facilitate endotracheal intubation, thereby increasing the likelihood of success and reducing potential injury to the patient. A field-of-view having an offset angle 311 is shown extending from an aperture (not shown) of the handle-side of the straight blade 304.

The connection 308 may include apertures 318a and 320a for images and light to be passed between the blade 304 and handle 302. The apertures 318a (defined by blade side surface of the handle) and 318b (defined by a handle side surface of the blade 304) (collectively aperture pair 318a/b) and corresponding apertures or aperture pair 320a/b are shown to be on the handle 302 and blade 304, and are aligned with one another such that light generated in the handle 302 and images captured in a scene pass between the handle 302 and blade 304, as further described with regard to FIGS. 3B and 3C. The apertures 318a/b and 320a/b are shown to be offset towards a side of the connection so as to be in alignment with channels 314 and 316 (see FIG. 3C) that extend along or within the blade 304. However, it should be understood that the positioning of the apertures 318a/b and 320a/b may be more centralized, and the channels 314 and 316 may have an alternative routing along the blade 304. As further shown, brackets 309a and 309b (collectively 309) that extend from and further define sidewalls of a blade side surface of the handle 302 to the sides of the connection 308 enable a proximal end of the blade 304 to be secured or connected to the handle 302 so that the apertures 318a/b and 320a/b are in respective alignment. The brackets 309 may be sized and shaped to operate as a friction fit for the blade 304. In an embodiment, a lock member (not shown), such as a moveable pin, ball, thumb screw, or otherwise, may be utilized to further secure the blade 304 with the handle 302. It should be understood that a wide variety of features may be utilized to connect or attach the handle 302 and blade 304.

Figure 3B:
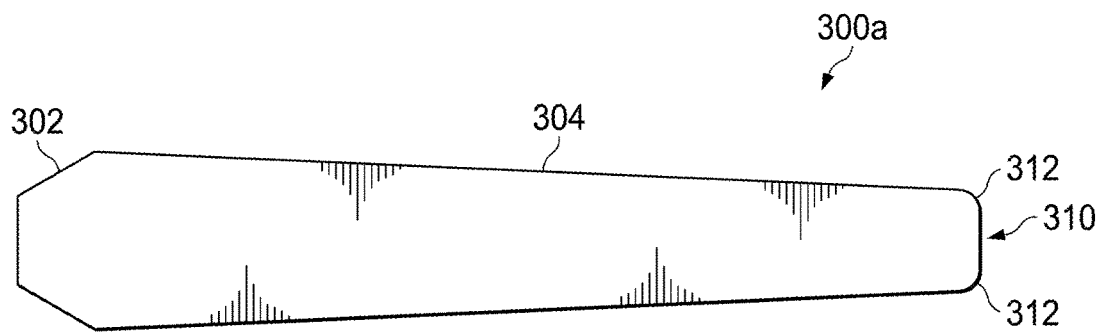

With regard to FIG. 3B, a top view illustration of the laryngoscope 300a of FIG. 3A is shown. The blade 304 is shown to taper from the handle 302 towards the distal end or tip 310. In an embodiment, the base end may have a width of approximately 21 mm and taper to approximately 12 mm with a length of approximately 125 mm extending from a front edge of the handle 302. To minimize risk of injury to a patient, the corners 312 of the tip 310 may be rounded. It should be understood that alternative lengths, widths, and/or thicknesses may be utilized depending on demographics of a patient on which the blade 304 may be utilized. For example, an blade 304 to be used with an infant may have different dimensions (e.g., shorter and narrower) than a blade 304 to be used with an adult male. In an embodiment, the proximal end of blades with different dimensions may have a common proximal end such that the connection 308 region of the handle 302 and blade 304 is the same, and also so the connection features are universal irrespective of the dimensions of the remainder of the blade 304. That is, by having the proximal end of blades with different dimensions, each can be utilized by a single handle 302, thereby providing blade flexibility for a medical professional.

Figure 3C:
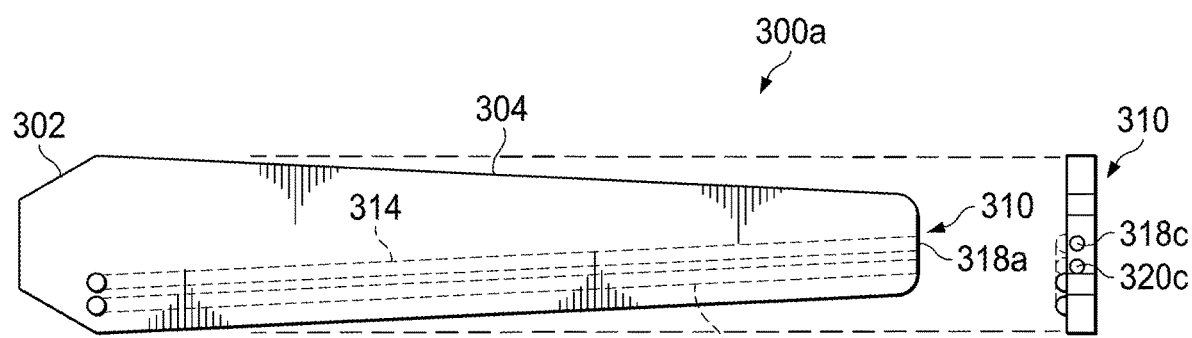

With regard to FIG. 3C, a bottom view illustration of the laryngoscope 300a of FIG. 3A shows that the laryngoscope blade 304 has a pair of channels, including a camera/video channel 314 and light channel 316 to enable the laryngoscope 300a to capture well-illuminated images/video while performing a laryngoscopy. In the embodiment, the channels extend along the left side of the laryngoscope blade 304. The channels 314 and 316 may be defined by the blade 304 itself or may be attached to the blade 304 (e.g., light tubes that extend along a handle side surface of the blade 304). In an embodiment, the blade 304 may be made of medical safe metal or any other material (e.g., plastic) and be rigid enough to engage and maintain a tongue away from a viewing area. The blade 304 may also be disposable and/or be capable of being sterilized. As further shown, a front view shows two apertures 318c and 320c to respectively enable images to be captured therethrough and light to be projected therefrom at an offset angle as images and light pass into and from the respective channels 314 and 316 that extend between the respective apertures 318a/b and 318c and apertures 320a/b and 320c. In an embodiment, the aperture(s) may have optical component(s), such as a prism, reflector, lens(es), etc., disposed to cause the images to have a certain field-of-view and/or view angle (e.g., between about 10 and about 40 degrees) and or project light with a certain angle and/or beamwidth. Being about 10 degrees and about 40 degrees may be slightly above or slightly below 10 degrees and 40 degrees (e.g., 10 degrees+/−2 degrees and 40 degrees+/−4 degrees). The angles may be fixed or may be manually or electromechanically set by a manufacturer or operator.

Figure 3D:
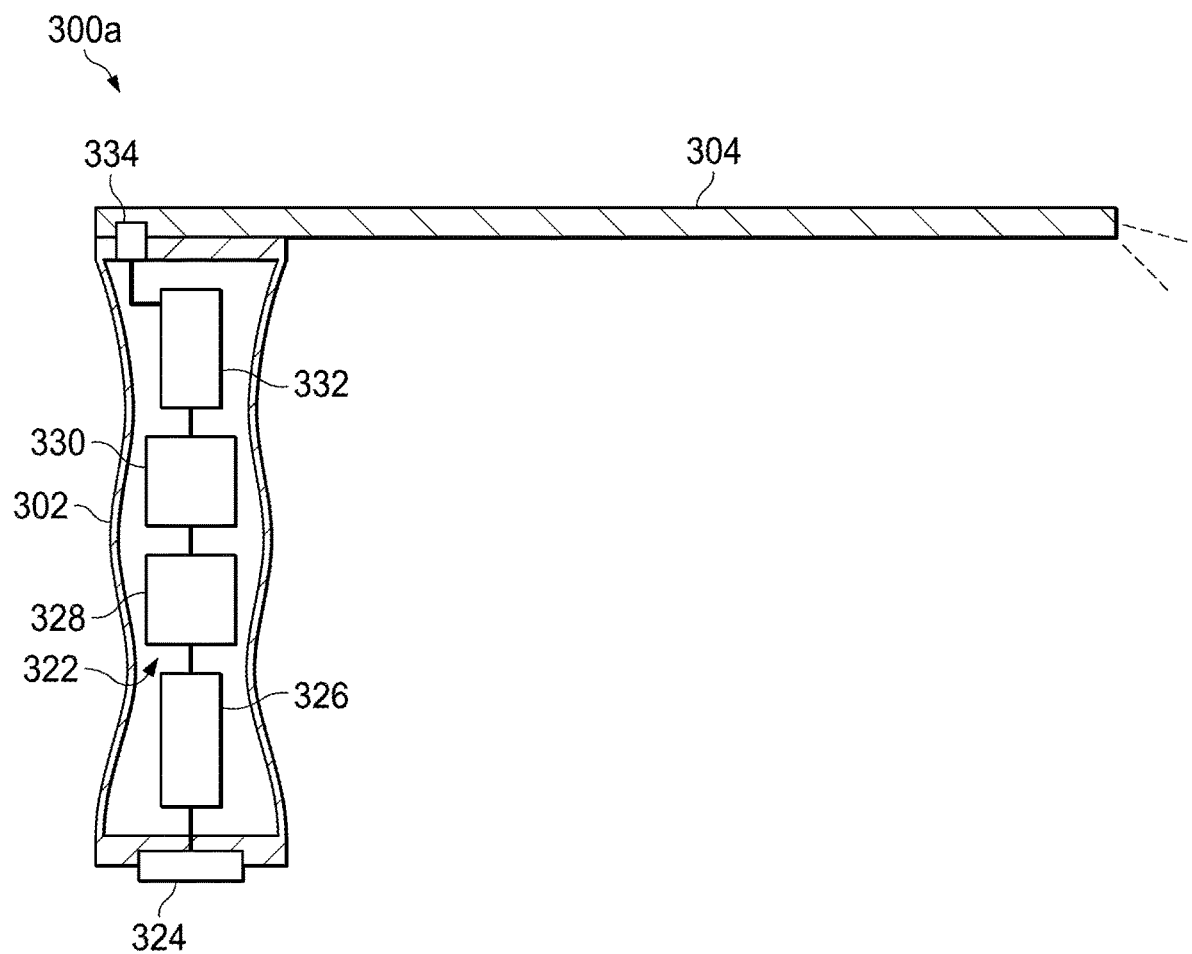

With regard to FIG. 3D, a side view illustration of the laryngoscope 300a showing illustrative electronics and optical components 322 within the handle 302 is shown. The electronics may include a power button 324, power source 326 (e.g., battery, such as a rechargeable battery), light source 328, camera or video electronics 330 (e.g., image sensor and video processor), wireless transmitter 332, and antenna 334. It should be understood that electrical conductors, such as a databus, and optical pathways, such as a fiber optic line, connectors, and so forth may also be included in the handle and as part of an interface with the blade 304. The interface may be defined by corresponding features (e.g., aligned apertures, electrical connectors or pads, snaps) on the handle 302 and the blade 304. By utilizing wireless communications, a wired connection with a remote computer may be eliminated and remote assistance to a medical professional may be provided. Moreover, a remote computer and data repository (e.g., on the "cloud") may store images collected by the laryngoscope 300a so as to make imaging records available to other emergency services (e.g., emergency room at a hospital) and preserve the imaging records to assist with future needs of the patent and/or medical professional (e.g., insurance, liability, etc.).

Figure 3E:
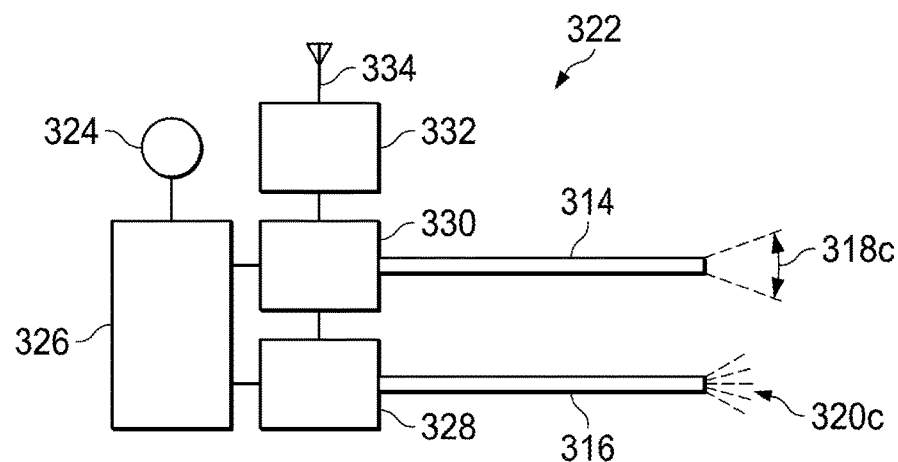

With regard to FIG. 3E, another view of the electronics and optics 322 is shown. The electronics, including the power button 324, battery 326, light source 328, camera 330, wireless transmitter 332, and antenna 334. The light source 328 may illuminate a scene via the light channel 316 and via the light aperture 320c, and camera 330 may receive images via the camera channel 314 and camera aperture 318c. As shown, the camera aperture 318c may enable a field-of-view angle of about 20 degrees (e.g., 20+/−2 degrees). It should be understood that alternative field-of-view angles may be utilized or that the field-of-view angle may be adjustable. The light aperture 320c may output light at approximate the same field-of-view angle as the camera aperture 318c. That is, the light may illuminate the scene in an overlapping manner so that the image being captured is fully illuminated. It should also be understood that the angle of the camera aperture 318c and light aperture 320c may be at an orientation that is offset from the longitudinal axis of the blade, as described with regard to FIG. 2.

Although the handle is shown to have the light source 328 therein, an alternative embodiment may include a light source within or at the distal end of the blade 304. In such a configuration, rather than using the light channel 316 to extend through the blade 304, an electrical conductor (not shown) may conduct power from the battery 326 to the light source 328. And, rather than having apertures 320a/b, an electrical connector pair (not shown) would be provided at the connector 308 on both the handle 302 and blade 304. Other similar arrangements of the camera 330 are also contemplated.

In an alternative embodiment, rather than the width (y-axis) and/or height (z-axis) being linearly tapered, alternative shapes that provide for the same or similar functionality may be provided. For example, the blade may be bulbous at or near the proximal end and optionally taper towards the tip. In another embodiment, the blade may be wide at the proximal end, extend with parallel edges towards the tip, flair or have flanges, and then taper or have parallel edges to the tip. Again, the blade may have a number of different configurations, but provide for the same or similar functionality as described herein with regard to lifting and compressing the tongue so as to provide for visual access to the airway by having an camera at an offset angle relative to the longitudinal axis of the straight blade. The blade may have another other geometric or non-geometric shape(s) in the lateral direction (y-axis) while being straight and thin.

Along the z-axis, the blade may be flat, tapered, or have any other shape(s) while providing for the same or similar functionality as described herein.

Figure 3F:
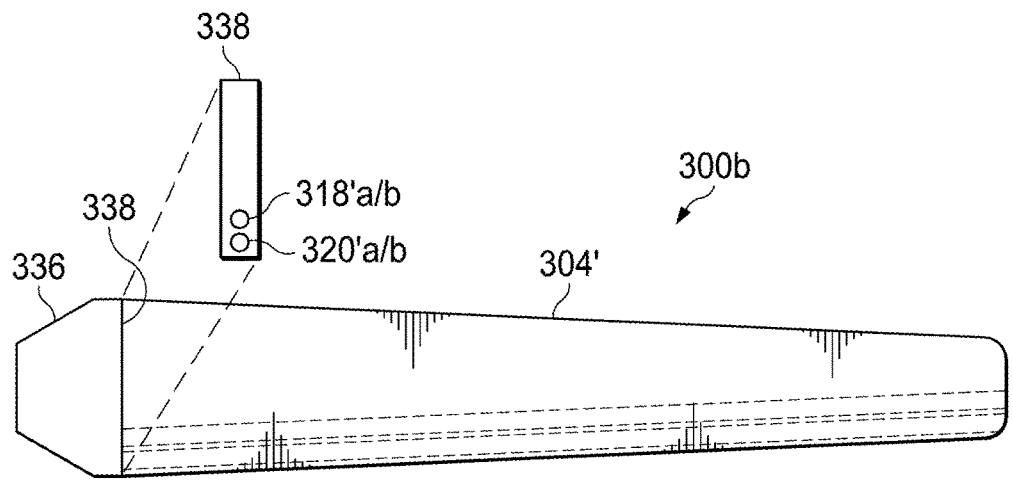
FIG. 3F is an illustration of an alternative embodiment of a laryngoscope.

With regard to FIG. 3F, an alternative embodiment of a laryngoscope 300b is shown. In this embodiment, rather than the connector for the blade being positioned at one end of the handle 302 (FIG. 3C), a blade adapter 336 may be configured to extend from the handle 302 or be part of the handle itself to enable an end of a blade 304' to be connected into the blade adapter 336 at a connector 338. In this case, apertures 318'a/b and 320'a/b are on the ends of the blade adapter 336 and blade 304', respectively. Using a direct alignment configuration may help simplify optics of the blade 304'. The blade adapter 336 may be permanently affixed or removably attached to the handle 302. A number of attachment mechanisms may be utilized, such as snaps, screws, friction fit, clips, clamps, or otherwise, which provide for a secure connection such that the blade 304' and blade adapter 336 are held together and have minimal or no "play" between one another. Once connected, the handle 302 and blade 304' are rigidly connected to one another such that a medical professional may use the laryngoscope 300b without concern that the two components will unexpectedly separate from one another.

Figure 4A:
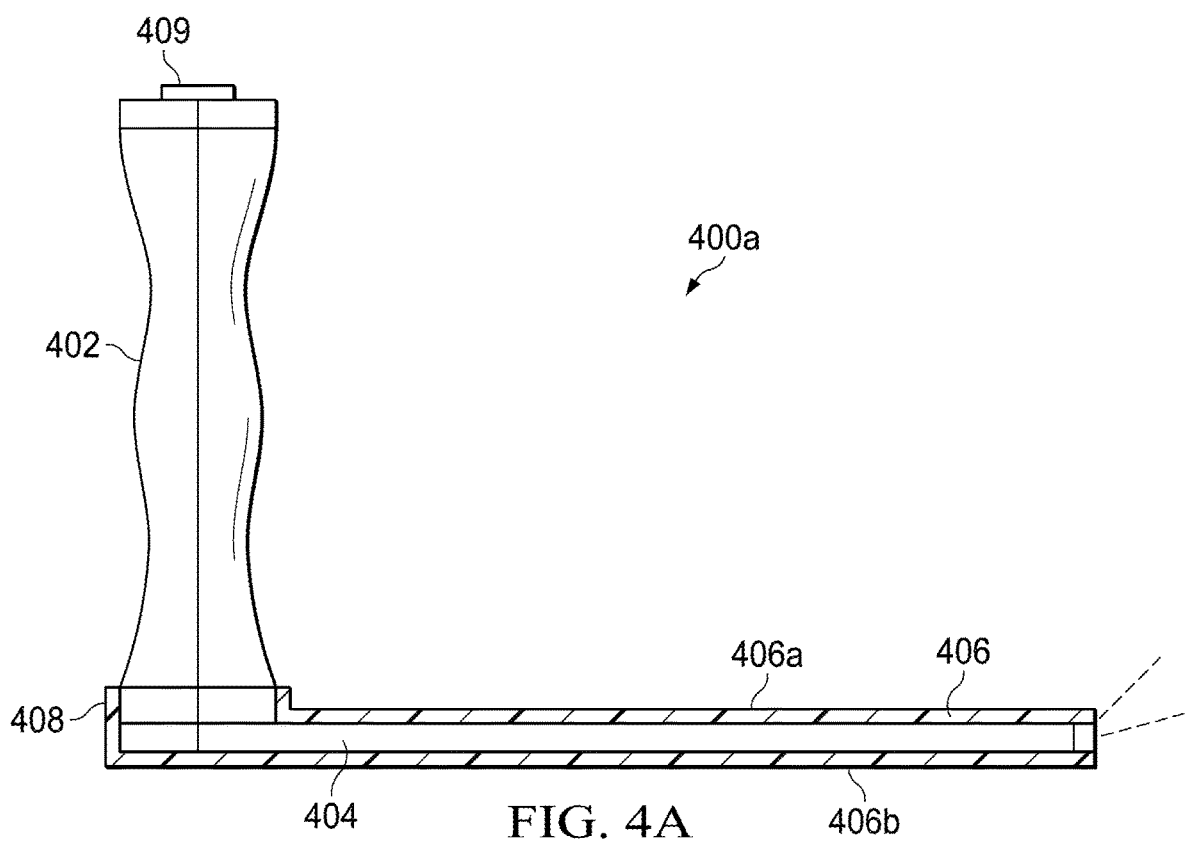
FIG. 4A is an illustration of an illustrative laryngoscope shown to include a handle blade, and disposable cover.
Figure 4B:
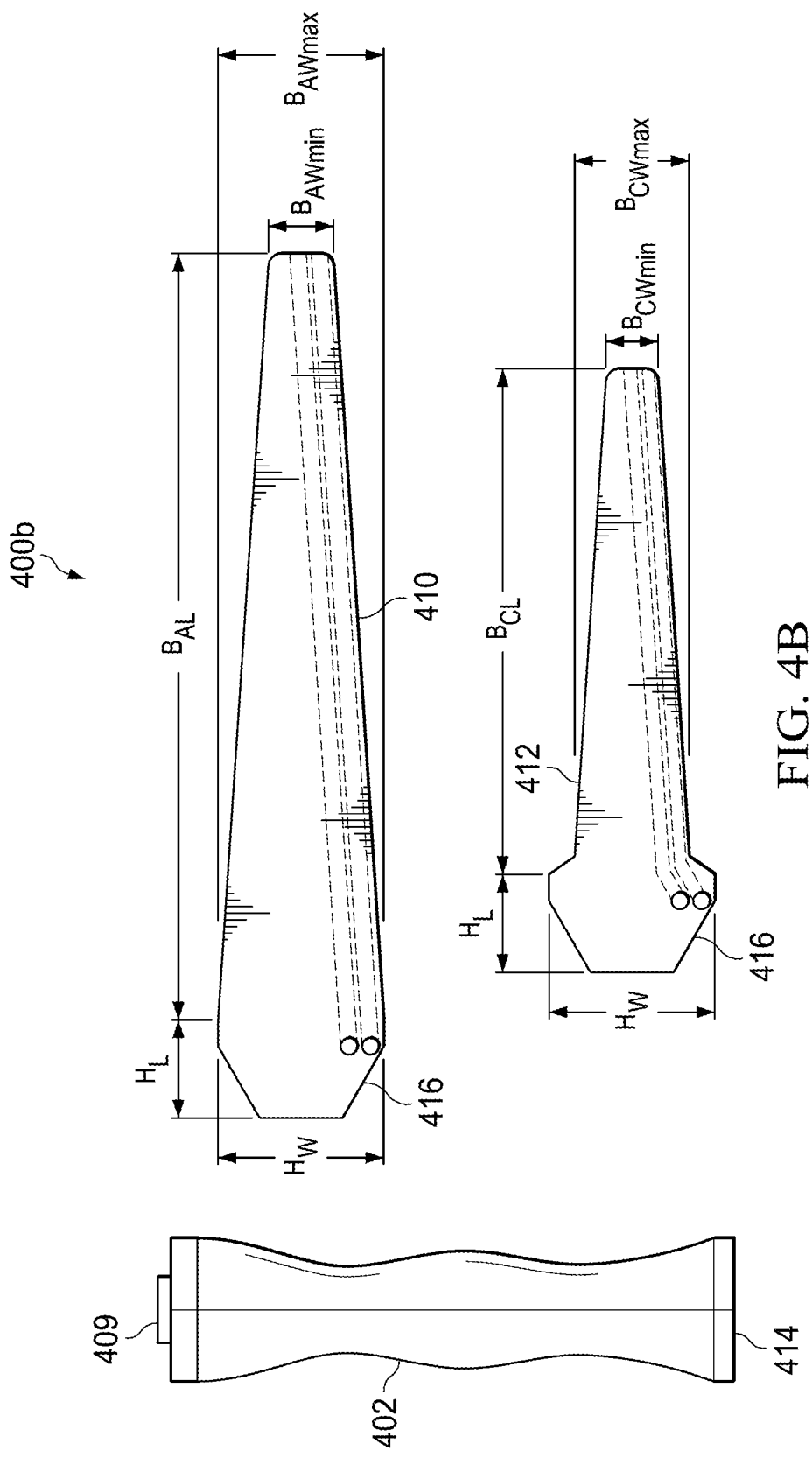
FIG. 4B is an illustration of an alternative embodiment of a laryngoscope kit that includes a common handle and blades of different sizes, but with a common head that interfaces with the handle.
Figure 5A:
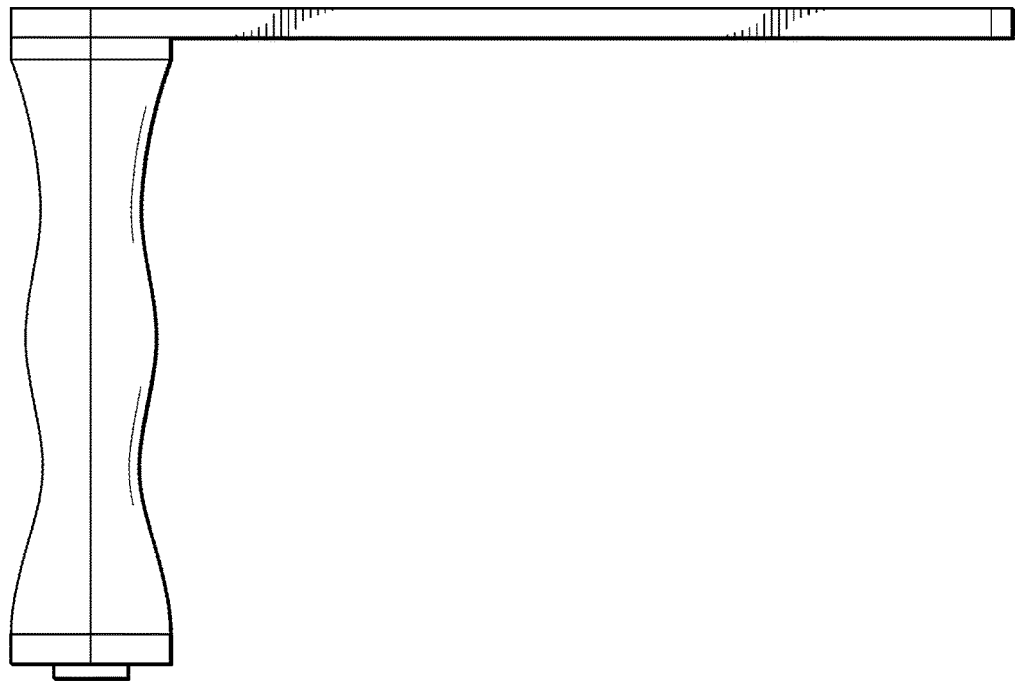
FIG. 5 are illustrations of a composite view of the components of a laryngoscope.
Figure 5B:
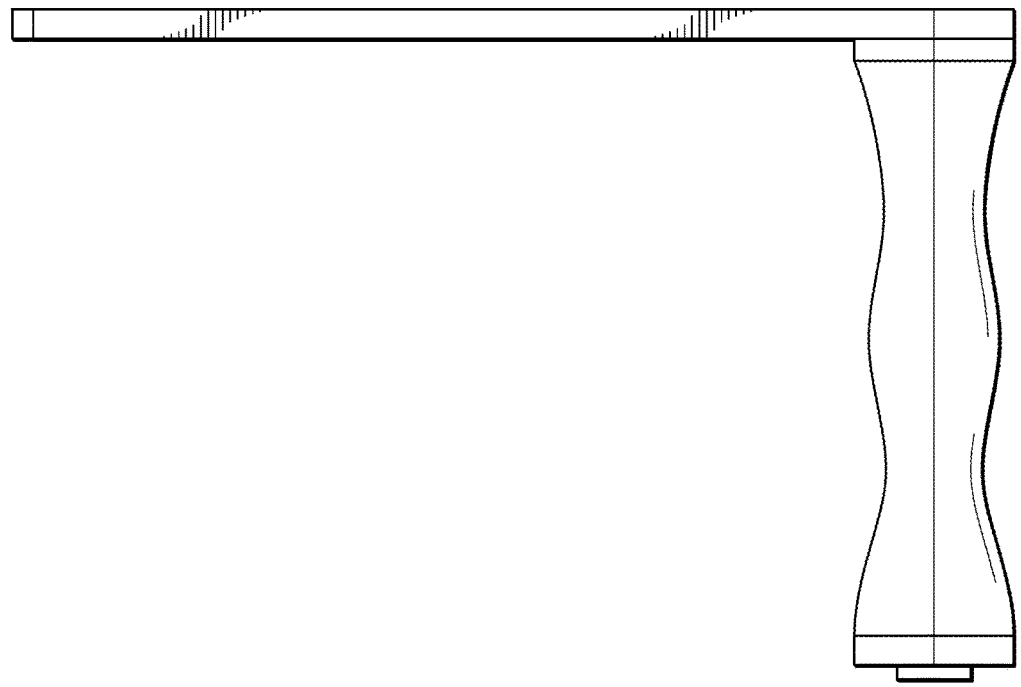
Figure 5C:
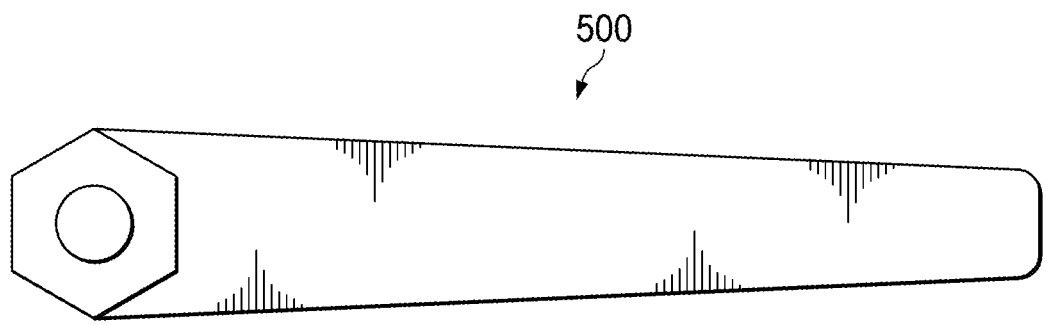
Figure 5D:
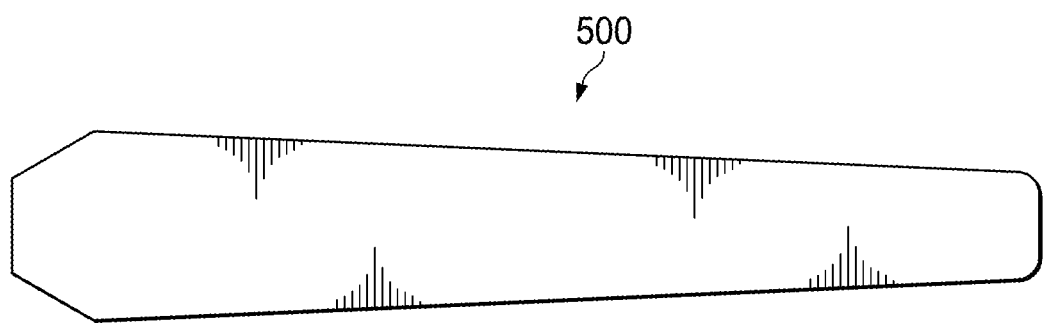
Figure 5E:
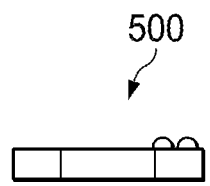
Figure 5F:
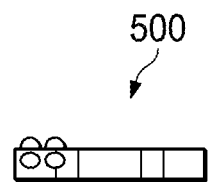

With regard to FIG. 4, an illustration of an illustrative laryngoscope 400 is shown to include a handle 402, blade 404, and disposable cover 406. The disposable cover 406 may be formed of plastic or other oral sanitary material and includes an interior cover surface and superior cover surface 406a and 406b. The disposable cover 406 may slide onto the blade 404 or extend over the blade 404 in a number of other ways. In an embodiment, the cover may attach to the handle at an attachment region 408 to help ensure the cover 406 does not separate from the laryngoscope 400 during use. The width of the tip of the cover 406 may be about 3 mm wide, and may taper in the same or similar proportions as the taper of the blade 404. Other widths and configurations of the blade 404 and cover 406 may also be utilized depending on the demographics and measurements of the patient. For example, a smaller and narrower blade 404 and cover 406 may be used for a child versus an adult. A quick release and connect mechanism(s) between the blade 404 and handle 402 may be provided. In an embodiment, the cover 406 may be configured to cover both the blade 404 and portion or entire handle 402.

A power button 409 may be disposed at an end of the handle 402 opposite the blade 404 such that a user's thumb may be able to activate and deactivate electronics within the handle 402 of the laryngoscope 400 during use. In an embodiment, rather than being on the very end of the handle 402, the button 409 may be positioned on the side wall of the handle 402 near the end, but such that a user may activate and deactivate the electronics. It should be understood that the button may be a push-button, a touch-sensitive button, a button configured with a biometric sensor (e.g., thumbprint sensor), switch, or any other electromechanical or electro-optical device that enables a user to turn ON or OFF the electronics of the laryngoscope 400. The button 409 may be engaged to perform other functions, such as start video, stop video, capture still image, etc. by performing a touch or activation sequence (e.g., double tap, triple tap, touch for a minimum duration of time, etc.).

With regard to FIG. 5, illustrations of a composite view of the components of a laryngoscope 500 are shown. It should be understood that the dimensions and features are illustrative, such that the camera and light apertures extending away from the blade in the blade side view may not be raised due to being formed and defined by a sidewall of the blade.

Figure 6:
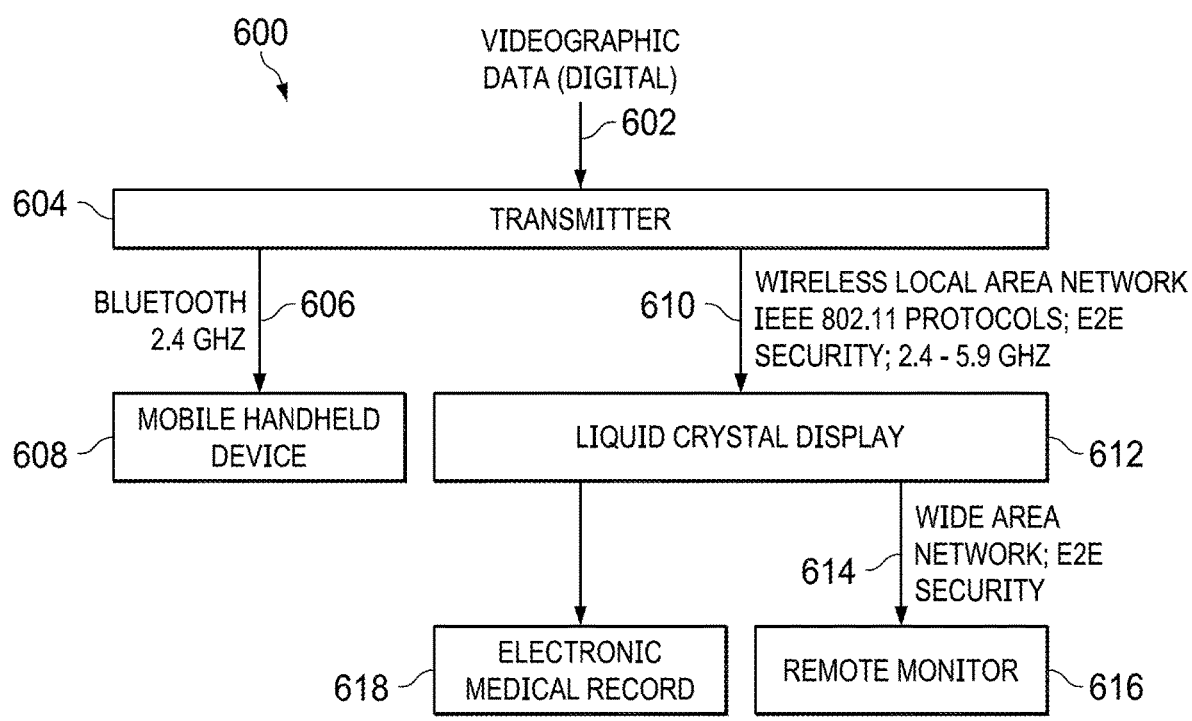
FIG. 6 is a flow diagram of an illustrative data flow process using a laryngoscope.

With regard to FIG. 6, a flow diagram of an illustrative data flow process 600 is shown. The process 600 may start at step 602, where video graphic data may be captured by an image sensor and processor, for example. The video graphic data may be processed by the image processor and communicated via wireless transmitter 604 using a local wireless communications protocol, such as Bluetooth, as wireless data 606 to a mobile handheld device 608. The mobile handheld device 608 may be a mobile telephone, such as a smart phone, tablet, or any other handheld device, as understood in the art. The transmitter 604 may additionally and/or alternatively communicate using a wireless local area network (LAN) (e.g., 802.11 communications protocol or any other wireless LAN communications protocol) at step 610.

A user of the laryngoscope may initiate a communication between the wireless transmitter 604 and mobile handheld device 608 by pressing a button to turn on the electronics of the laryngoscope. A synchronization process may occur to synchronize or pair so that the laryngoscope and mobile handheld device 608 communicate using the communications protocol. To ensure secure communications are made due to data from the laryngoscope being medical data, a single or double authentication process may occur. For example, the user may be asked to enter a password, perform a biometric verification (e.g., supply a thumbprint, perform facial recognition, and/or otherwise) on the mobile handheld device 608 and/or laryngoscope to initiate the communications in a secure manner (e.g., encrypted communications). In an embodiment, the authentication process may be made each time the laryngoscope is turned on. Alternatively, the secure pairing process may last for a predetermined time period (e.g., one hour) so that the user does not need to perform the secure pairing too often. Other techniques for securely pairing the laryngoscope and the mobile handheld device 608 may be utilized.

The data transmitted by the transmitter may be communicated to an electronic display 612, such as a liquid crystal display (LCD). It should further be understood that the image data may be communicated via a wide area network (WAN), such as via a mobile communications network. In an embodiment, the mobile handheld device 608 may be configured with a secure software application (app) that is configured to enable a microphone of the device 608 to capture audible sounds and synchronize captured audible data with captured video data being received from the laryngoscope. The audio and video data may be communicated wirelessly to a remote location via a communications channel (e.g., via the Internet and/or mobile network, for example) for real-time feedback and/or storage. A remote location may include an electronic device of a medical professional who may provide guidance or other audible feedback to an airway manager via the app on the device 608.

The electronic display 612 may display the data thereon. In an embodiment, a processor in communication with the electronic display 612 may process and format the data for a user to view. In an embodiment, the data may be communicated via a WAN at step 614 to a remote monitor 616, where a medical professional may monitor the images being captured real time and provide immediate and ongoing verbal feedback to an airway manager performing a laryngoscopy. Moreover, the data may be communicated to an electronic medical record (EMR) 618 for storage. The electronic medical record 618 may be used by medical professionals to review the laryngoscopy by caregivers, for example, or for insurance purposes. It should be understood that real-time image data collected during a laryngoscopy may be used for a variety of different purposes. It should further be understood that the process of FIG. 6 is illustrative, and that a wide variety of alternative processes and sub-processes may be utilized in addition to or in conjunction with the process 600.

A mobile app being executed on the mobile electronic device may be configured with security features, such as encryption, to comply with state and federal privacy laws. Still yet, the mobile app may support collecting video data and/or still image data and synchronize audio data collected from a microphone on the mobile electronic device and communicate that combined data via a local or wide area network to a remote location for storage and/or feedback from a medical professional in a real-time manner. That data may be stored for use by an emergency room team, for example, or for insurance or other purposes thereafter.

One embodiment of a method of manufacturing a laryngoscope may include forming a blade being straight and having a handle side and a non-handle side. The blade extends from a proximal end to a distal end, and may be configured to connect to a handle at the proximal end. A first channel configured to enable light signals to pass therethrough through the blade may be formed, where the first channel may include (i) a first aperture disposed at the proximal end of the first channel and (ii) a second aperture disposed at the distal end of the first channel. A second channel configured to enable optical signals to pass therethrough may be formed, the second channel may include (i) a third aperture disposed at the proximal end of the second channel and (ii) a fourth aperture disposed at the distal end of the second channel, where the fourth aperture may be oriented at an offset angle such that images captured via the fourth aperture are at the offset angle on or toward the handle side of the blade.

The process may further include forming the handle including an interface inclusive of fifth and sixth apertures aligned with the first and second apertures of the blade when connected thereto, and be configured to be connected to the blade at the proximal end and extend from the handle side of the blade, where extending from the handle side means that the handle may be connected to the proximal end of the blade in a linear direction, but extend toward and from the handle side of the blade). The handle may define a cavity in which electronics are positioned. The electronics may be positioned in the cavity of the handle, where the electronics include a battery, illumination source, and camera. The illumination source may be positioned in optical communication with the fifth and first apertures, and be configured to generate an illumination signal that projects into the first channel via the fifth and first apertures and out of the second aperture to illuminate a scene. The camera may be positioned in optical communication with the sixth and third apertures, and be configured to capture images that are collected via the fourth aperture, second channel, third aperture, and sixth aperture.

A lens may be connected at the fourth aperture, whereby a line-of-sight of the lens is in alignment with the line-of-sight of the fourth aperture. A first fiber optic line may be inserted to extend between the first aperture and second aperture via the first channel. A second fiber optic line may be inserted to extend between the third aperture and fourth aperture via the second channel, and configured to communicate optical signals of a scene along the line-of-sight of the lens.

The process may further include positioning the electronics includes positioning wireless communications electronics configured to wirelessly communicate image signals captured by the camera. Forming the second channel may include forming the second channel with the offset angle of the fourth aperture being between approximately 10 degrees and approximately 40 degrees. Forming the second aperture may include forming the second aperture at approximately the same offset angle as the fourth aperture. Forming the straight blade may include forming the straight blade with side edges along surfaces of the handle and non-handle sides so as to define a latitudinal profile, and wherein the latitudinal profile tapers from the proximal end to the distal end.

Forming the straight blade may include forming the straight blade with a ratio of the taper along the latitudinal profile being approximately 2:1. Forming the straight blade may include forming the straight blade with surfaces on the handle and non-handle sides so as to define a vertical profile that tapers from the proximal end to the distal end. A disposable cover that extends over the blade and handle may be formed.

An embodiment of a laryngoscope may include a blade being straight and having handle and non-handle sides. The blade extends from a proximal end to a distal end. A handle may be configured to be connected to the blade at the proximal end and extend in a direction on or towards the handle side of the blade. The handle may define a cavity in which electronics are positioned. An illumination source may be configured to illuminate a scene. A camera may be configured to capture images of the scene illuminated by the illumination source, the scene may be at an offset angle on or towards the handle side of the blade.

The blade may define a first channel and a second channel, where the illumination source may be positioned within the cavity of the handle and be configured to illuminate an illumination signal through the first channel to be projected at the offset angle from the blade. The camera may be positioned within the cavity of the handle and be configured to capture images via the second channel of the scene. In an embodiment, the offset angle is between approximately 10 degrees and approximately 40 degrees. The straight blade may have side edges along the handle and non-handles sides of the blade so as to define a latitudinal profile, and wherein the latitudinal profile tapers from the proximal end to the distal end. A ratio of the taper of the straight blade along the latitudinal profile may be approximately 2:1. The straight blade has handle and non-handle side surfaces so as to define a vertical profile, and the vertical profile may taper from the proximal end to the distal end.

A laryngoscope kit may include a handle configured to be connected to one of a plurality of blades. The handle may define a cavity in which electronics are positioned, the electronics including a camera and an illumination source. A first blade may be straight and have a handle side and a non-handle side. The first blade extends from a proximal end to a distal end, and may be defined by a connection region having first dimensions and blade region having second dimensions. The first blade may further define a first channel and a second channel with respective first and second apertures at the distal end of the first blade, the first and second apertures may have an offset angle on or towards the handle side of the first blade. A second blade may be straight and have a handle side and a non-handle side. The second blade extends from a proximal end to a distal end, and defined by a connection region having the first dimensions and blade region having third dimensions. The second blade may further define a third channel and a fourth channel with respective third and fourth apertures at the distal end of the second blade. The third and fourth apertures may have an offset angle on or towards the handle side of the second blade. The illumination source may be configured to illuminate a scene via the first and third channels and first and third apertures when respective first and second blades are connected to the handle. A camera may be configured to capture images of the scene via the second and fourth channels and second and fourth apertures when respective first and second blades are connected to the handle. In addition to a kit including a handle and multiple sized blades, additional blades may be sold as individual blades, packages of common sized blades, and pages of different sized blades.

The previous description is of at least one embodiment for implementing the invention, and the scope of the invention should not necessarily be limited by this description. The scope of the present invention is instead defined by the following claims.

What is claimed is:

1. A laryngoscope, comprising:
    a blade being straight and having a handle side and a non-handle side, the straight blade extending from a proximal end to a distal end, the straight blade defining:
        a first channel configured to enable light to pass therethrough, the first channel extending from the proximal end to the distal end of the blade;
        a first aperture disposed at the proximal end of the first channel;
        a second aperture disposed at the distal end of the first channel;
        a second channel configured to enable optical images to pass therethrough, the second channel extending from the proximal end to the distal end of the straight blade;
        a third aperture disposed at the proximal end of the second channel; and
        a fourth aperture disposed at the distal end of the second channel, the fourth aperture (i) positioned on a distal-most end surface of the blade and (ii) oriented at an offset angle on or toward the handle side of the straight blade such that line-of-sight images captured via the fourth aperture are at the offset angle;
    a handle connected to the straight blade at the proximal end and extending from the handle-side of the straight blade, the handle defining a cavity in which electronics are positioned and fifth and sixth apertures in a connector surface at which the straight blade connects with the handle, the electronics including a battery, illumination source, and camera;
    the illumination source being in optical communication with the fifth and first apertures, and configured to generate an illumination signal that projects into the first channel and out of the second aperture to illuminate a scene; and
    the camera being in optical communication with the sixth and third apertures, the camera being configured to capture images in the line-of-sight and at the offset angle of the fourth aperture and via the fourth aperture, second channel, third aperture, and sixth aperture.

2. The laryngoscope according to claim 1, further comprising a lens disposed at the fourth aperture, wherein line-of-sight of the lens is in alignment with the orientation of the fourth aperture.

3. The laryngoscope according to claim 2, further comprising:
    a first fiber optic line extending between the first aperture and second aperture via the first channel; and
    a second fiber optic line extending between the third aperture and fourth aperture via the second channel, and configured to communicate optical signals of a scene along the line-of-sight of the lens.

4. The laryngoscope according to claim 1, wherein the electronics further include wireless communications electronics configured to wirelessly communicate image signals captured by the camera.

5. The laryngoscope according to claim 1, wherein the electronics further include wireless communications electronics that are configured to communicate the image signals in real-time.

6. The laryngoscope according to claim 5, wherein the wireless communications electronics are further configured to communicate the image signals to a local electronics device to cause the local electronics device to synchronize audible signals with image signals in real-time so as to communicate the synchronized data therefrom.

7. The laryngoscope according to claim 1, wherein the offset angle is between approximately 10 degrees and approximately 40 degrees.

8. The laryngoscope according to claim 7, wherein the offset angle is approximately 20 degrees.

9. The laryngoscope according to claim 1, wherein the second aperture enables the illumination signal to be projected from the blade at approximately the same offset angle at which the images are captured.

10. The laryngoscope according to claim 1, wherein the straight blade has side edges between surfaces on handle and non-handle side surfaces so as to define a horizontal profile, and wherein the horizontal profile tapers from the proximal end to the distal end.

11. The laryngoscope according to claim 10, wherein a ratio of the taper of the straight blade along the horizontal profile is approximately 2:1.

12. The laryngoscope according to claim 1, wherein the straight blade has handle side and non-handle side surfaces so as to define a vertical profile, and wherein the vertical profile tapers from the proximal end to the distal end.

13. The laryngoscope according to claim 1, further comprising a disposable cover that extends over the straight blade and handle.

* * * * *